(12) United States Patent
Henderson et al.

(10) Patent No.: US 11,957,879 B2
(45) Date of Patent: Apr. 16, 2024

(54) AUTOINJECTOR

(71) Applicant: SANOFI-AVENTIS DEUTSCHLAND GMBH, Frankfurt am Main (DE)

(72) Inventors: Charley Henderson, Cambridgeshire (GB); David Cross, Hertfordshire (GB); Douglas Ivan Jennings, Hertfordshire (GB); Ryan Anthony McGinley, Cambridgeshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/218,884

(22) Filed: Jul. 6, 2023

(65) Prior Publication Data

US 2023/0347054 A1   Nov. 2, 2023

Related U.S. Application Data

(63) Continuation of application No. 17/726,381, filed on Apr. 21, 2022, which is a continuation of application
(Continued)

(30) Foreign Application Priority Data

Nov. 6, 2012   (EP) .................................... 12191442

(51) Int. Cl.
*A61M 5/20* (2006.01)
*A61M 5/31* (2006.01)
(Continued)

(52) U.S. Cl.
CPC ........ *A61M 5/2033* (2013.01); *A61M 5/3129* (2013.01); *A61M 5/3245* (2013.01);
(Continued)

(58) Field of Classification Search
CPC .............. A61M 5/2033; A61M 5/3245; A61M 5/3129; A61M 2005/208; A61M 2205/60;
(Continued)

(56) References Cited

U.S. PATENT DOCUMENTS 4,020,836 A   5/1977  Cunningham
4,430,079 A   2/1984  Thill et al.
(Continued)

FOREIGN PATENT DOCUMENTS

CN   1713930    12/2005
CN   102271736  12/2011
(Continued)

OTHER PUBLICATIONS

Extended European Search Report in Application No. 12191442.8, dated Apr. 16, 2013, 5 pages.
(Continued)

*Primary Examiner* — Lauren P Farrar
(74) *Attorney, Agent, or Firm* — Fish & Richardson P.C.

(57) ABSTRACT

An autoinjector includes a case configured to receive a syringe, a slidable member that is movable axially within the case to cause at least a portion of the syringe to move axially when the syringe is disposed within the case for dispensing a medicament through a needle of the syringe, a locking member configured to prevent actuation of the slidable member when the autoinjector is in a pre-dispense configuration, a sleeve coupled to a distal end of the case and surrounding at least a portion of a needle of the syringe when the syringe is disposed within the case, an elongate member extending proximally from the sleeve and configured to deflect the locking member to allow actuation of the plunger, and two drive springs coupled to the slidable member and configured to apply a biasing force that acts on the slidable member to move the slidable member distally.

29 Claims, 17 Drawing Sheets

Related U.S. Application Data

No. 16/507,291, filed on Jul. 10, 2019, now Pat. No. 11,344,676, which is a continuation of application No. 14/440,819, filed as application No. PCT/EP2013/072897 on Nov. 4, 2013, now Pat. No. 10,391,246.

(51) Int. Cl.
  *A61M 5/32* (2006.01)
  *A61M 5/46* (2006.01)

(52) U.S. Cl.
  CPC . *A61M 2005/202* (2013.01); *A61M 2005/206* (2013.01); *A61M 2005/208* (2013.01); *A61M 2005/314* (2013.01); *A61M 5/3202* (2013.01); *A61M 5/3204* (2013.01); *A61M 2005/3247* (2013.01); *A61M 5/326* (2013.01); *A61M 5/46* (2013.01); *A61M 2205/3368* (2013.01); *A61M 2205/581* (2013.01); *A61M 2205/582* (2013.01); *A61M 2205/583* (2013.01); *A61M 2205/586* (2013.01); *A61M 2205/60* (2013.01); *A61M 2205/6009* (2013.01)

(58) Field of Classification Search
  CPC ...... A61M 2205/583; A61M 2205/582; A61M 2205/581; A61M 2005/3247; A61M 2205/6009; A61M 2205/586; A61M 2005/206; A61M 2005/202; A61M 5/46; A61M 5/326; A61M 5/3202; A61M 5/3204; A61M 2005/314
  See application file for complete search history.

(56) References Cited

U.S. PATENT DOCUMENTS

| | | | |
|---|---|---|---|
| 4,681,566 | A | 7/1987 | Fenton et al. |
| 6,099,503 | A | 8/2000 | Stradella |
| 7,717,877 | B2 | 5/2010 | Lavi et al. |
| 7,955,304 | B2 | 6/2011 | Guillermo |
| 7,976,499 | B2 | 7/2011 | Grunhut et al. |
| 8,409,138 | B2 | 4/2013 | James et al. |
| 8,690,836 | B2 | 4/2014 | Mathews et al. |
| 10,391,246 | B2 | 8/2019 | Henderson et al. |
| 11,344,676 | B2 | 5/2022 | Henderson et al. |
| 2003/0171717 | A1* | 9/2003 | Farrugia ............ A61M 5/2033 604/131 |
| 2005/0288633 | A1 | 12/2005 | Jeffrey |
| 2006/0229559 | A1 | 10/2006 | Marano-Ford et al. |
| 2010/0137808 | A1 | 6/2010 | Wilmot et al. |
| 2011/0106008 | A1 | 5/2011 | Kronestedt |
| 2011/0123314 | A1 | 9/2011 | Guillermo |
| 2011/0224620 | A1* | 9/2011 | Johansen ............ A61M 5/2033 604/192 |
| 2011/0319860 | A1 | 12/2011 | Williamson et al. |
| 2012/0035542 | A1 | 2/2012 | Pongprairochana |
| 2012/0123350 | A1 | 5/2012 | Lucio et al. |
| 2012/0209192 | A1 | 8/2012 | Alexandersson |
| 2015/0297833 | A1 | 10/2015 | Henderson et al. |
| 2019/0328972 | A1 | 10/2019 | Henderson et al. |
| 2022/0241507 | A1 | 8/2022 | Henderson et al. |

FOREIGN PATENT DOCUMENTS

| | | |
|---|---|---|
| EP | 0615762 | 9/1994 |
| EP | 2253348 | 11/2010 |
| EP | 2357013 | 8/2011 |
| EP | 2364741 | 9/2011 |
| EP | 2468328 | 6/2012 |
| EP | 2468340 | 6/2012 |
| EP | 2468341 | 6/2012 |
| JP | S54-152606 U | 10/1979 |
| JP | S54-155000 U | 10/1979 |
| JP | 2000-510021 | 8/2000 |
| JP | 2007-534345 | 11/2007 |
| JP | 2012-502764 | 2/2012 |
| JP | 2012-509717 | 4/2012 |
| JP | 2013-521084 | 6/2013 |
| JP | 2014-502876 | 2/2014 |
| JP | 2014-502887 | 2/2014 |
| JP | 2014-506159 | 3/2014 |
| WO | WO 1998/015307 | 4/1998 |
| WO | WO 2004/054644 | 7/2004 |
| WO | WO 2004/112871 | 12/2004 |
| WO | WO 2009/037141 | 3/2009 |
| WO | WO 2009/083600 | 7/2009 |
| WO | WO 2010/033806 | 3/2010 |
| WO | WO 2010/049239 | 5/2010 |
| WO | WO 2010/068415 | 6/2010 |
| WO | WO 2011/005177 | 1/2011 |
| WO | WO 2011/032956 | 3/2011 |
| WO | WO 2011/043714 | 4/2011 |
| WO | WO 2011/110466 | 9/2011 |
| WO | WO 2012/072559 | 6/2012 |
| WO | WO 2012/085019 | 6/2012 |
| WO | WO 2012/085029 | 6/2012 |
| WO | WO 2012/085032 | 6/2012 |

OTHER PUBLICATIONS

International Preliminary Report on Patentability in International Application No. PCT/EP2013/072897, dated May 12, 2015, 7 pages.

International Search Report and Written Opinion in International Application No. PCT/EP2013/072897, dated Feb. 2, 2014, 9 pages.

Rote Liste, "50. Hypophysen—, Hypothalamushormone, andere regulatorische Peptide u. ihre Hemmstoffe," Chapter 50, ed. 2008, 20 pages.

* cited by examiner

AUTOINJECTOR

This application is a continuation of U.S. patent application Ser. No. 17/726,381, filed Apr. 21, 2022, which is a continuation of U.S. patent application Ser. No. 16/507,291, filed Jul. 10, 2019, now U.S. Pat. No. 11,344,676, which is a continuation of U.S. patent application Ser. No. 14/440,819, filed May 5, 2015, now U.S. Pat. No. 10,391,246, which is a 371 U.S. National Application of PCT/EP2013/072897, filed on Nov. 4, 2013, which claims priority to European Patent Application No. 12191442.8, filed on Nov. 6, 2012, the entire contents of which are incorporated herein by reference.

TECHNICAL FIELD

The disclosure relates to an autoinjector for administering a medicament.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Conventional electro-mechanical or fully electronic autoinjectors may not be as robust as fully mechanical autoinjectors. For example, electro-mechanical or fully electronic autoinjectors may include batteries which require replacement and may be more difficult or impossible to fix if a component breaks.

Thus, there remains a need for an improved autoinjector.

SUMMARY

The present disclosure provides an improved autoinjector.

In an exemplary embodiment, an autoinjector according to the present disclosure includes a case, a door hingedly coupled to the case and having an open position and a closed position, a plunger slidably disposed in the case, and at least one drive spring applying a biasing force on the plunger relative to the case. The door is operably coupled to the plunger, and rotation of the door from the closed position to the open position moves the plunger from a distal position in the case to a proximal position in the case and compresses the at least one drive spring.

In an exemplary embodiment, an autoinjector according to the present disclosure further includes a trigger button disposed on the case and operably coupled to the plunger.

In an exemplary embodiment, an autoinjector according to the present disclosure further includes an interlock sleeve slidably disposed in the case and having an extended position and a retracted position relative to the case. The interlock sleeve includes at least one interlock beam extending axially in the case. In an exemplary embodiment, an autoinjector according to the present disclosure further includes at least one resilient button locking beam disposed in the case and adapted to engage the at least one interlock beam. The interlock beam causes the button locking beam to deflect when the interlock sleeve is in the retracted position.

In an exemplary embodiment, an autoinjector according to the present disclosure further includes at least one trigger button beam operably coupled to the trigger button, and the at least one trigger button beam abuts the at least one button locking beam when the interlock sleeve is in the extended position. The at least one trigger button beam causes the at least one tongue to disengage the ratchet face when the trigger button is actuated and the interlock sleeve is in the retracted position.

In an exemplary embodiment, the plunger includes a transverse beam, a piston rod extending from the transverse beam, and at least one leg extending from the transverse beam and parallel to the piston rod. The at least one leg includes a distal foot adapted to support the at least one drive spring. The at least one leg includes a ratchet face having a plurality of teeth. In an exemplary embodiment, an autoinjector according to the present disclosure further includes at least one resilient tongue disposed in the case and having a hook adapted to engage a tooth on the ratchet face.

In an exemplary embodiment, an autoinjector according to the present disclosure further includes at least one lever hingedly coupled to the door, and at least one roller rotatably coupled to the lever. The roller is disposed in a track formed in the case.

In an exemplary embodiment, an autoinjector according to the present disclosure further includes a retraction collar adapted to engage a needle boot on a syringe. When the door is rotated from the open position to the closed position, the at least one lever engages the retraction collar to push the needle boot at least partially through an aperture of the interlock sleeve.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound includes at least one peptide for the treatment and/or prophylaxis of diabetes mellitus or complications associated with diabetes mellitus such as diabetic retinopathy, wherein in a further embodiment the pharmaceutically active compound includes at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2, or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while p and a have approximately 550 amino acids. Each heavy chain has two regions, the constant region (CH) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Other embodiments will become apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

Figure 1:
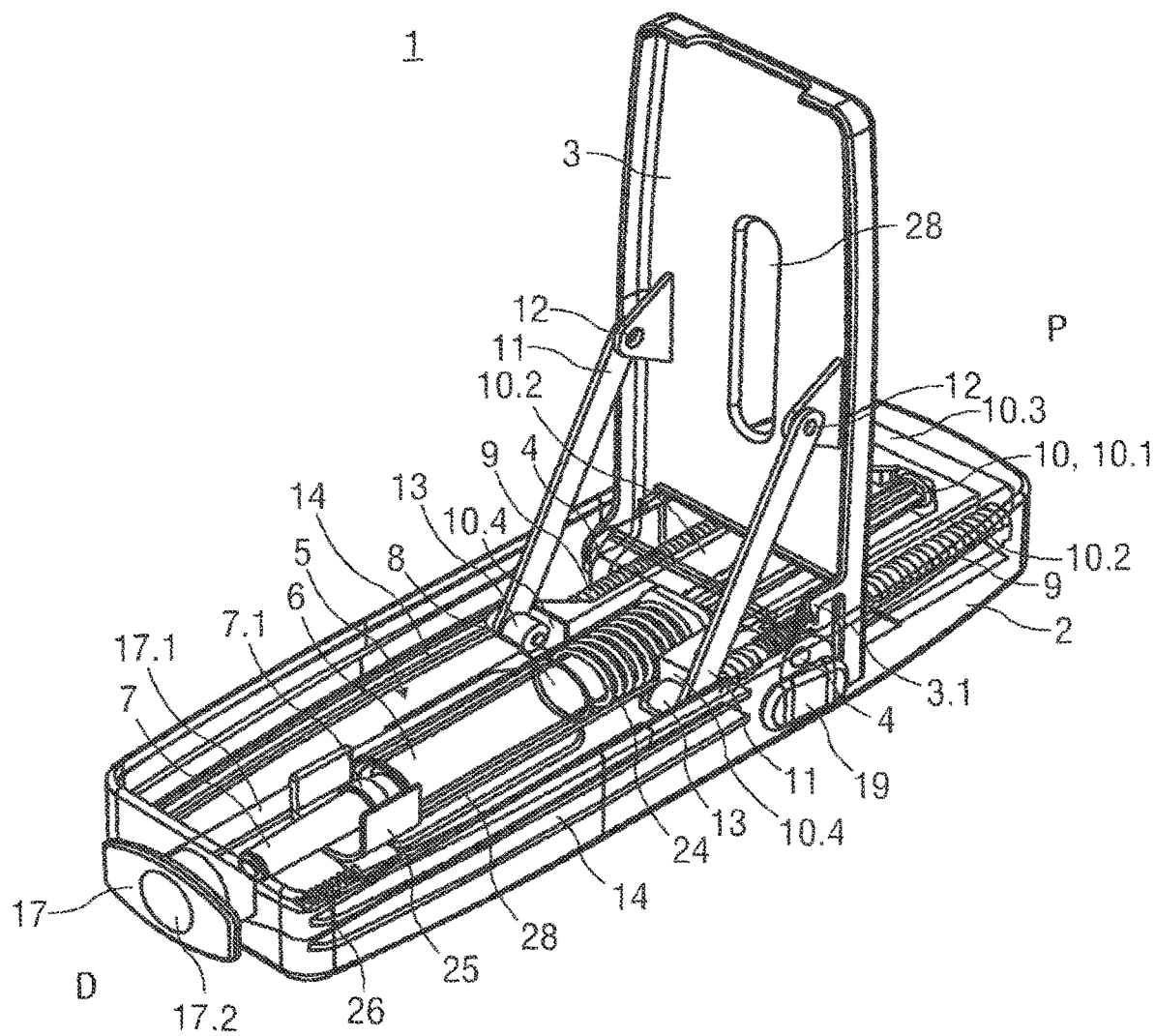
FIG. 1 is a perspective view of an exemplary embodiment of an autoinjector according to the present disclosure.

FIG. 1 is a perspective semitransparent view of an exemplary embodiment of an autoinjector 1 according to the present disclosure.

In an exemplary embodiment, the autoinjector 1 includes a case 2 designed to be held by a patient, health-care provider or other user during an injection. The case 2 may have a generally elongate, rectangular shape and may include one or more ergonomic features (e.g., finger grooves for gripping) and/or textured surfaces or skins for preventing a user's hand from slipping while using the autoinjector 1.

In an exemplary embodiment, the case 2 includes a door 3 which is configurable in an open position or a closed position. In the open position, the door 3 provides access to a syringe carrier in the case 2 that is adapted to hold a syringe 6 or a cartridge containing a medicament. In the closed position, the door 3 may be locked. As shown in the exemplary embodiment in FIG. 1, the door 3 may be formed on a side of the case 2 and rotate about a transverse hinge between the open and closed positions. However, those of skill in the art will understand that the door 3 may be formed on any side or face of the case 2 and may rotate, slide or translate relative to the case 2 to open and close.

In an exemplary embodiment, a door spring may be arranged in the case 2 to bias the door 3 to the open position. A door latch may be formed on the case 2 and/or the door 3 to maintain the door 3 in the closed position. In an exemplary embodiment, the door latch may be rotated or deflected to engage/disengage the case 2 and/or the door 3 to allow the door 3 to open and close. When the door 3 is in the open position, a used syringe may be removed from the syringe carrier and a new syringe may be inserted into the syringe carrier.

In an exemplary embodiment, at least one drive spring 9 is disposed in the case 2. In the exemplary embodiment shown in FIG. 1, two drive springs 9 are compression springs disposed in parallel in the case 2. Those of skill in the art will understand that other exemplary embodiments may utilize a single drive spring, and one or more tension or torsion drive springs.

In an exemplary embodiment, the drive springs 9 apply a biasing force on a plunger 10. The plunger 10 includes a piston rod 10.1 projecting distally from a transverse beam 10.3 and two legs 10.2 projecting distally from opposing lateral portions of the transverse beam 10.3 and parallel to the piston rod 10.1. In the exemplary embodiment, each drive spring 9 is positioned between a proximal end of the case 2 and a distal foot 10.4 of each leg 10.2.

In an exemplary embodiment, at least one lever 11 is hingedly coupled to the door 3 at a first end via a pivot 12 and engages a roller 13 at a second end. The roller 13 may be disposed in an axial track 14 which is formed in the case 2, and the roller 13 may be adapted to engage the distal foot 10.4 of the leg 10.2 of the plunger 10 when the door 3 is moved from the closed position to the open position. In another exemplary embodiment, the second end of the lever 11 may engage the track 14 and be axially moveable relative thereto. A projection or abutment surface may be coupled to the second end of the lever 11 and adapted to engage the distal foot 10.4 of the leg 10.2. As explained further below, the door 3 and the levers 11 may be utilized as a reset mechanism.

Figure 2:
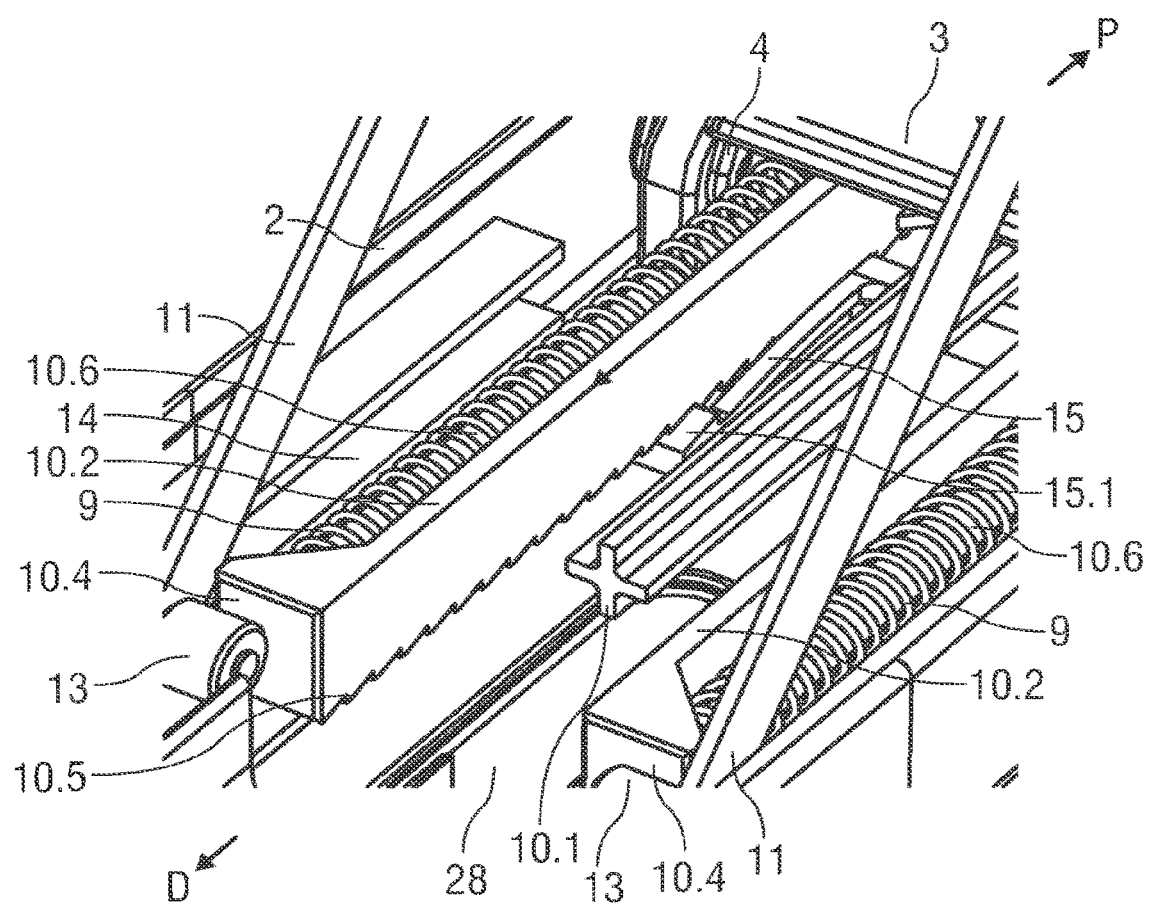
FIG. 2 is a perspective detail view of an exemplary embodiment of an autoinjector according to the present disclosure prior to use.

FIG. 2 shows an exemplary embodiment of an autoinjector 1 according to the present disclosure. In the exemplary embodiment shown in FIG. 2, the door 3 is in the opened position, and a roller 13 is abutting the distal foot 10.4 of each leg 10.2. In the exemplary embodiment, each leg 10.2 includes a ratchet face 10.5 having teeth that are adapted to engage a hook 15.1 on a resilient tongue 15. The tongue 15 may be an elongate member formed in the case 2 which is fixed at one end and deflectable at an opposite end having the hook 15.1, and the tongue 15 may be biased toward the leg 10.2. Thus, as the leg 10.2 is moving in the proximal direction, the teeth on the ratchet face 10.5 may engage the hook 15.1 to prevent the plunger 10 from moving in the distal direction during a reset operation and/or while moving the door 3 from the closed position to the open position. Those of skill in the art will understand that the teeth on the ratchet face 10.5 and the hook 15.1 may have corresponding ramped engagement surfaces to reduce a force required to open the door 3.

FIG. 2 also shows an exemplary embodiment of guide pins 10.6 which may be formed on a proximal end of the case 2 and project in a distal direction through holes in the transverse beam 10.3. The guide pins 10.6 may provide support and alignment for the drive springs 9.

Figure 3:
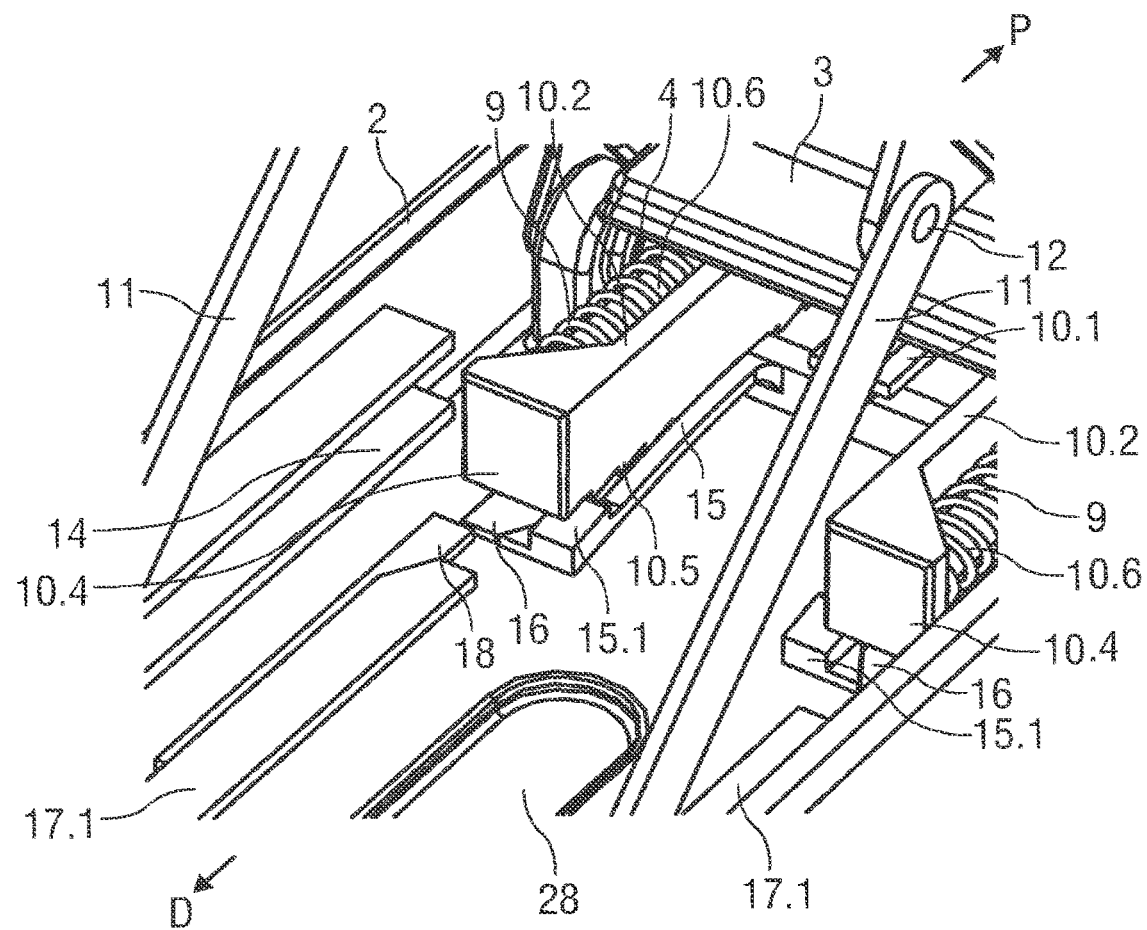
FIG. 3 is a perspective detail view of an exemplary embodiment of an autoinjector according to the present disclosure prior to use.

FIG. 3 shows an exemplary embodiment of an autoinjector 1 according to the present disclosure. In the exemplary embodiment shown in FIG. 3, the plunger 10 has been fully translated in the proximal direction P, the drive springs 9 have been compressed, the hooks 15.1 have engaged a distal-most tooth on each ratchet face 10.5, and the door 3 is being closed.

Referring again to FIG. 1, the autoinjector 1 includes a trigger button (not visible in the figures) arranged on the case 2. The trigger button serves for starting an injection process when actuated. The trigger button may be a push button, a switch, a dial (e.g., to vary needle penetration depth), etc. The trigger button may be arranged on a proximal end of the case 2 or a side of the case. In another exemplary embodiment, the trigger button may be replaced by a push-actuated device, which is actuated when the autoinjector 1 is placed on the injection site. In an exemplary embodiment, a spring biases the trigger button relative to the case 2.

In an exemplary embodiment, the autoinjector 1 includes an interlock sleeve 17 slidably disposed in the case 2. The interlock sleeve 17 includes a distal end which protrudes from an aperture formed in a distal end of the case 2. The distal end of the interlock sleeve 17 includes an aperture 17.2 for allowing a needle to pass through during needle insertion into the injection site. The distal end of the interlock sleeve 17 may further include an expanded contact face to support proper alignment of the autoinjector 1 on the injection site and provide additional stability during the injection.

The interlock sleeve 17 may be biased by a spring in an extended position, which position is shown in the exemplary embodiment in FIG. 1. When the autoinjector 1 is placed on the injection site, interlock sleeve 17 may be pushed in the proximal direction into a retracted position against the biasing force of the spring.

Figure 4:
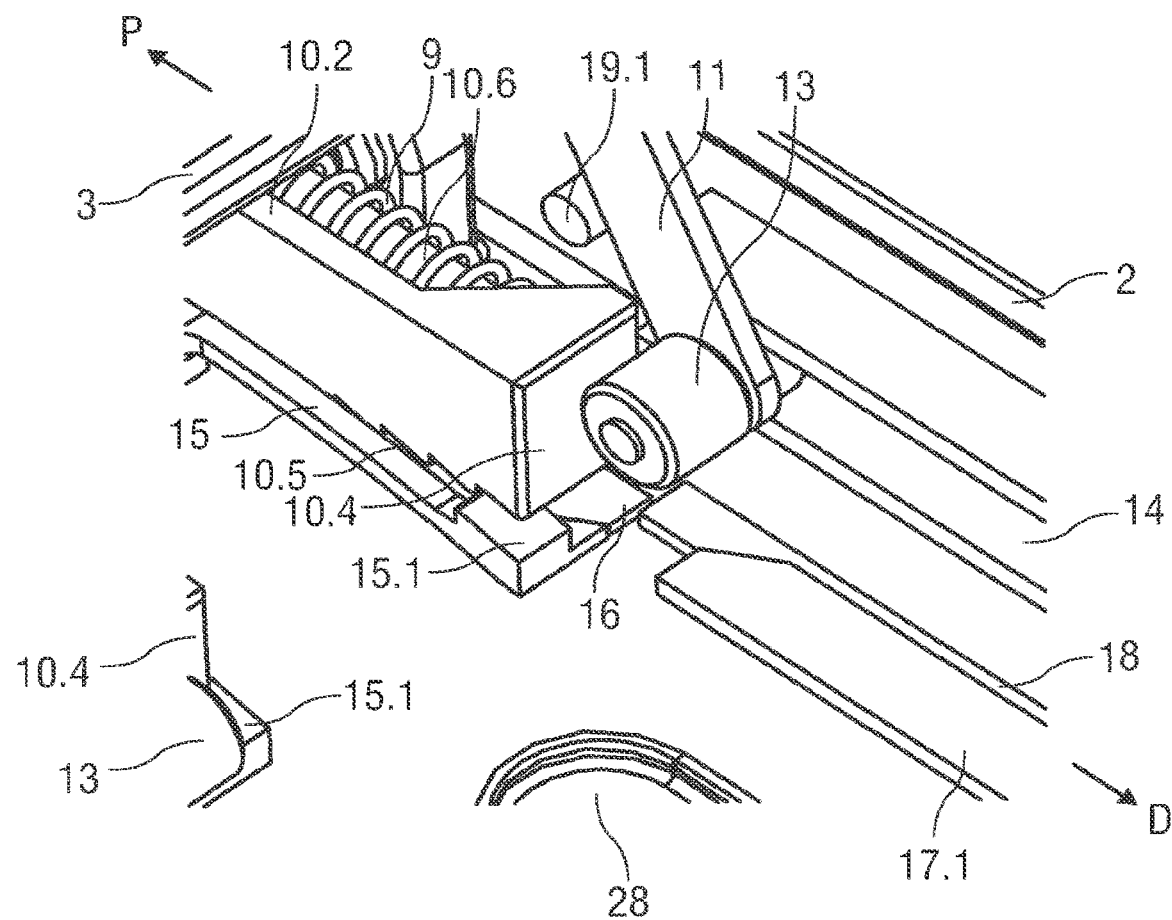
FIG. 4 is a perspective detail view of an exemplary embodiment of an autoinjector according to the present disclosure prior to use.

FIGS. 3 and 4 show an exemplary embodiment of the autoinjector 1 according to the present disclosure in which the trigger button is operably coupled to the interlock sleeve 17. For example, when the interlock sleeve 17 is in the extended position, the trigger button may be locked and prevented from actuation. When the interlock sleeve 17 is in the retracted position, the trigger button may be unlocked and actuatable.

In an exemplary embodiment, two interlock beams 17.1 extend in the proximal direction from the distal end of the interlock sleeve 17. In an exemplary embodiment, the interlock beams 17.1 are maintained on an inside of the case 2, and may include abutment surfaces which engage a distal end of the case 2 when the interlock sleeve 17 is in the extended position. Proximal ends of the interlock beams 17.1 include ramped surfaces which engage corresponding ramped surfaces of resilient button locking beams 18 disposed in the case 2. When the interlock sleeve 17 moves from the extended position to the retracted position, the proximal ends of the interlock beams 17.1 cause the button locking beams 18 to deflect.

In a non-deflected state, the button locking beams 18 are adapted to engage distal ends of trigger button beams 16, which are operably coupled to the trigger button, and prevent the trigger button beams 16 from moving in the distal direction. When the button locking beams 18 are deflected, the trigger button beams 16 may move in the distal direction. The distal ends of the trigger button beams 16 are in ramped engagement with the resilient tongues 15. Thus, axial movement of the trigger button beams 16 causes the resilient tongues 15 to deflect laterally and disengage the legs 10.2 of the plunger 10.

Thus, in the exemplary embodiment, the trigger button is actuatable when the interlock sleeve 17 is in the retracted position. Otherwise, the trigger button is prevented from actuation, because the button locking beams 18 abut the trigger button beams 16, as shown in FIGS. 3 and 4.

Referring again to FIG. 1, in an exemplary embodiment, a door lock 19 may be disposed on the case 2. The door lock 19 may be a button, a switch or other component which maintains the door 3 in the closed position. As shown in the exemplary embodiment in FIG. 4, the door lock 19 has a pin 19.1 which projects into the interior of the case 2. The door lock 19 may have a proximal position in which the pin 19.1 is disengages from a door hook 3.1 (shown in FIG. 1) and a distal position in which the pin 19.1 engages the door hook 3.1. The door lock 19 may be biased (e.g., by a spring) in the distal position, and when the door is moved from the open position to the closed position, a ramped portion of the door hook 3.1 may move the pin 19.1 and the door lock 19 into the proximal position until the door 3 is closed, and then the door lock 19 may return (under the biasing force) to the distal position so that the pin 19.1 engages the door hook 3.1 and locks the door 3.

Figure 5:
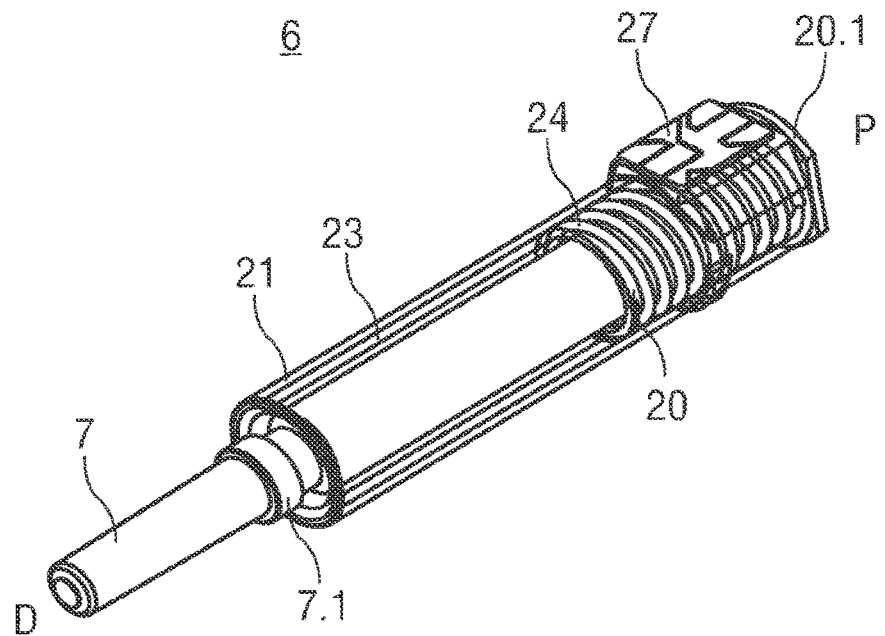
FIG. 5 is a perspective view of an exemplary embodiment of a syringe for use with an autoinjector according to the present disclosure.
Figure 6:
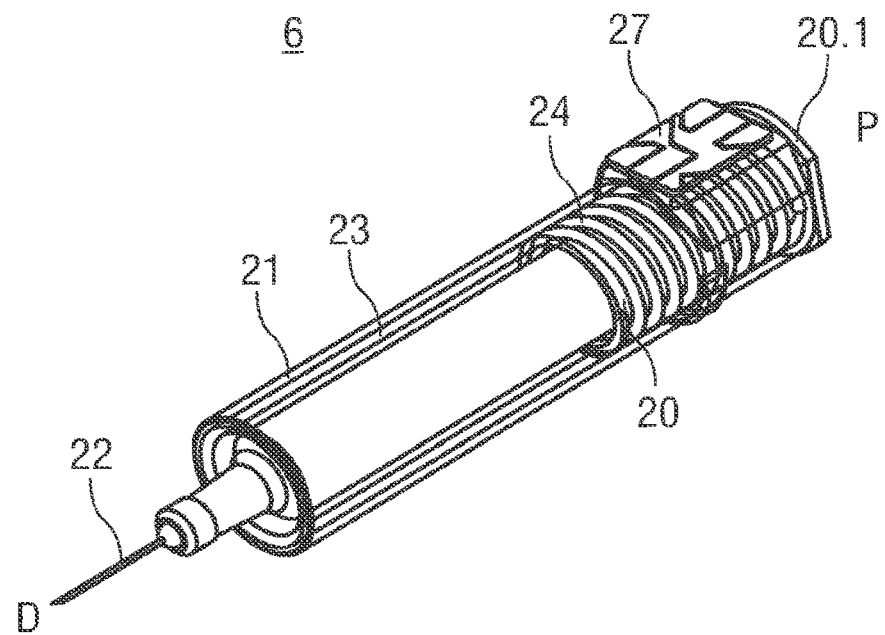
FIG. 6 is a perspective view of an exemplary embodiment of a syringe for use with an autoinjector according to the present disclosure.
Figure 7:
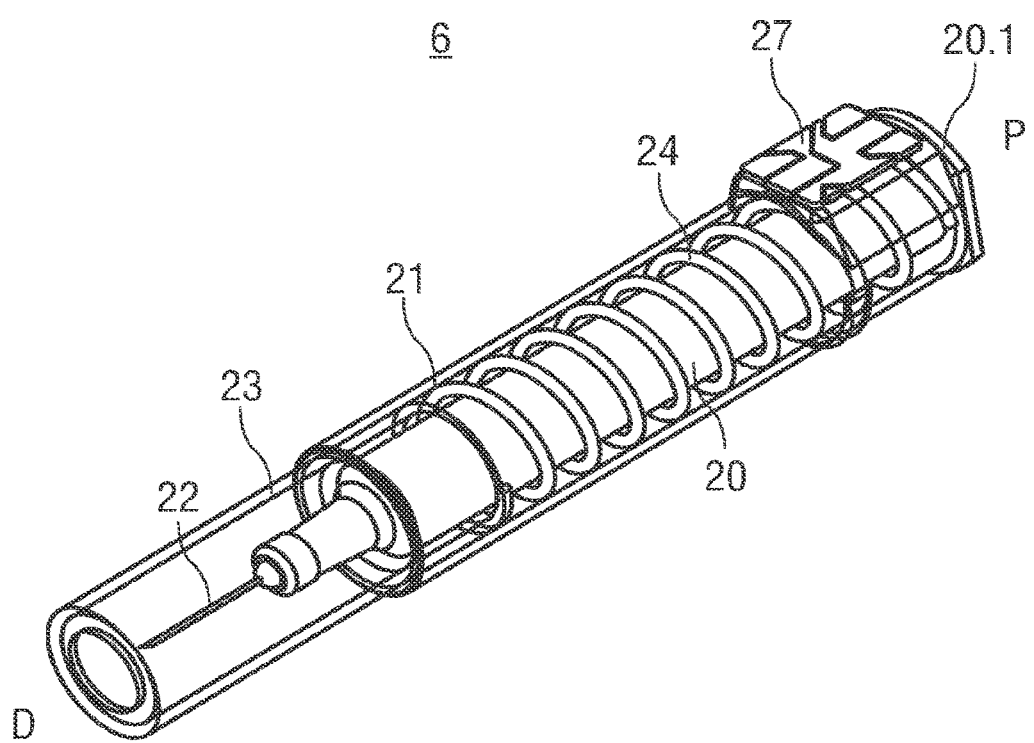
FIG. 7 is a perspective view of an exemplary embodiment of a syringe for use with an autoinjector according to the present disclosure.
Figure 16:
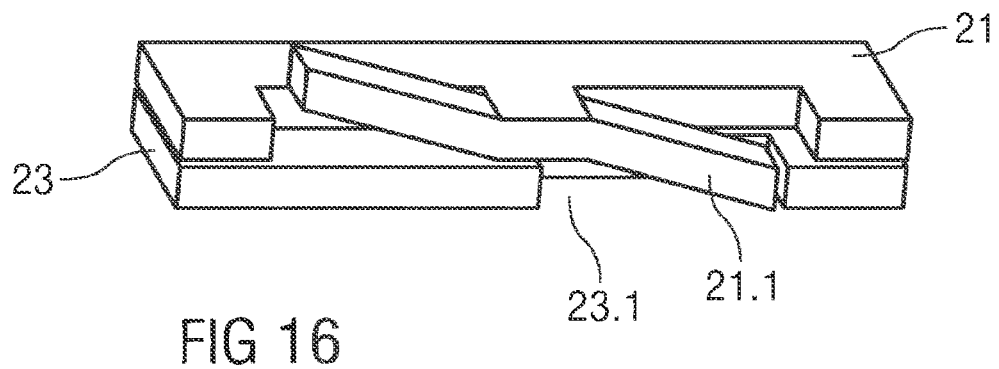
FIG. 16 is a perspective view of an exemplary embodiment of a needle shield release mechanism according to the present disclosure in a retracted position.
Figure 17:
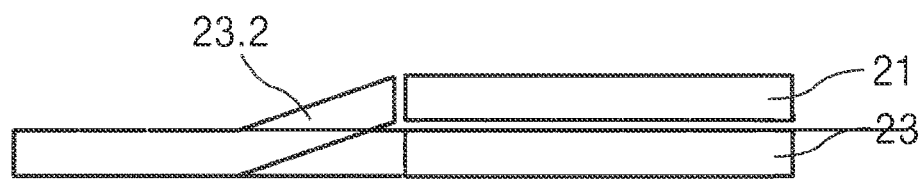
FIG. 17 is a perspective view of an exemplary embodiment of a needle shield according to the present disclosure in an extended position.

FIGS. 5-7 show an exemplary embodiment of a syringe 6 for use with the autoinjector 1 according to the present disclosure. The syringe 6 includes a body 20 containing a medicament and a case 21 telescopically coupled to the body 20. The case 21 may include an attachment (e.g., hooks, snaps, etc.) which engage a finger flange 20.1 on a proximal end of the body 20. A needle shield 23 is telescopically coupled to the case 21 and is biased toward the distal direction relative to the case 21 by a spring 24. The needle shield 23 is retained in its retracted state (shown in FIG. 16) by a pivoted clip 21.1 on the case 21 which in a non-deflected position engages a recess in the needle shield 23 and in a deflected position disengages the recess in the needle shield 23. Referring to FIG. 6, a needle 22 is disposed at a distal end of the body 20. A needle boot 7 is, as shown in FIG. 5, arranged on the needle 22, prior to use. FIG. 6 shows the syringe 6 with the needle boot 7 removed and the needle shield 23 in a retracted position, with the needle 22 exposed. FIG. 7 shows the syringe 6 with the needle shield 23 in an extended position, covering a distal tip of the needle 22. The needle shield 23 may be locked in its extended position, as shown in FIG. 17, by a resilient beam 23.2 which is released and abuts the case 21 once the shield 23 is in its fully extended position.

In an exemplary embodiment, a data storage device 27 may be disposed on the syringe 6 and include data, such as a type and volume of the medicament, filling and/or expiration date of the medicament, temperature of the medicament (e.g., if there is a temperature sensor on or near the syringe 4), a manufacturer of the medicament and/or the autoinjector 1, patient data (e.g., name, physician, dosing regiment, etc.), a used/unused indicator, etc. The data storage device 27 may interface with a wired or wireless communication device for transmitting the data to a computing device. The computing device may be used for tracking use/attributes of the syringe 6, e.g., for compliance and/or quality control purposes.

Referring again to FIG. 1, in an exemplary embodiment, the autoinjector 1 includes a retraction collar 25 distally supporting the syringe 6 and biased against the case 2 in the proximal direction P by a retraction spring 26 so that the syringe 6 is biased towards a retracted position in which the needle 22 is covered within the case 2.

Figure 18:
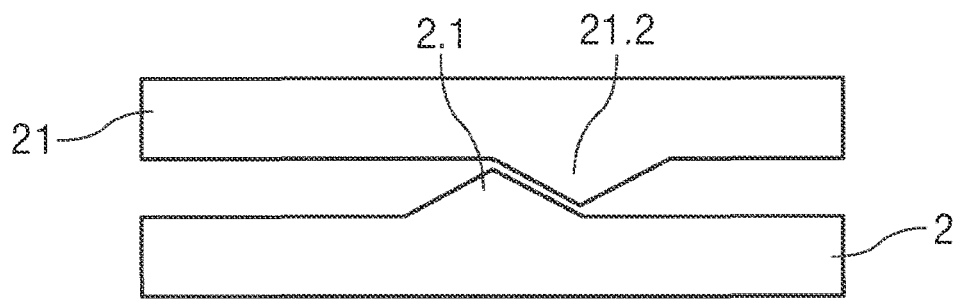
FIG. 18 is a perspective view of an exemplary embodiment of an engagement of a needle shield and a case of an autoinjector according to the present disclosure.

In an exemplary embodiment, the retraction collar 25 is utilized for removing the needle boot 7 prior to an injection. The retraction collar 25 includes a flange which is adapted to engage the needle boot 7. For example, the flange may engage a proximal surface on an annular boot collar 7.1 on the needle boot 7. In an exemplary embodiment, as the door 3 is moved from the open position to the closed position, when the door 3 is almost closed, the levers 11 and/or the rollers 13 may operably engage the retraction collar 25 to advance the retraction collar 25 in the distal direction, against the force of the retraction spring 26. The needle boot 7 may then be at least partially disengage from the needle 22 and at least partially exposed through the aperture 17.2 in the distal end of the interlock sleeve 17. As shown in FIG. 18, the syringe assembly 6 is held in place via interference between a boss 21.2 on the syringe case 21 and a ramped boss 2.1 on the case 2. The force to overcome the interference is higher than the forces generated as the door 3 is closed; however it is lower than the drive forces during device firing.

In an exemplary embodiment, the case 2 and/or the door 3 may include a viewing window 28 for allowing inspection of the syringe 6 and its contents and state.

In an exemplary, non-illustrated embodiment a distal end of the piston rod 10.1 may include resilient elements which may be inwardly deflected so as to reduce an external diameter of the distal end of the piston rod 10.1. In a relaxed position of the resilient elements, the external diameter of the distal end of the piston rod 10.1 is slightly greater than an internal diameter of the proximal end of the syringe body 20. The resilient elements may be rounded off or ramped so that they may be inwardly deflected when pushing on the proximal end of the syringe body 20 and when a counteracting force of the syringe body 20 exceeds a predetermined value. The proximal end of the syringe body 20 may exhibit an internal circumferential collar slightly reducing the internal diameter of the syringe body 20 and providing an additional detent which has to be overcome by the distal end of the piston rod 10.1 before it can enter the syringe body 20. If the piston rod 10.1 is advanced in the distal direction, it contacts the collar. As long as the syringe body 20 can move in the distal direction the counteracting force from the syringe body 20 may be too low to deflect the resilient elements. Hence, the piston rod 10.1 advances the syringe body and the whole syringe for extending the needle 22 from the case 2 without pushing on the stopper 8. As the syringe 6 advances the retraction spring 26 is compressed. When the needle 22 has reached its insertion depth the syringe 6 bottoms out against a stop in the case 2 thereby suddenly increasing the counteracting force opposing the force from the piston rod 10.1. The resilient elements are therefore inwardly deflected by the collar disengaging the piston rod 10.1 from the syringe body 20 and allowing it to advance further and engage the stopper 8 for displacing the medicament from the syringe body 20.

An exemplary sequence of operation of the autoinjector 1 is described in the following, though those of skill in the art will understand that various steps in the sequence may be conducted in any order and is not limited to the sequence described below.

Figure 8:
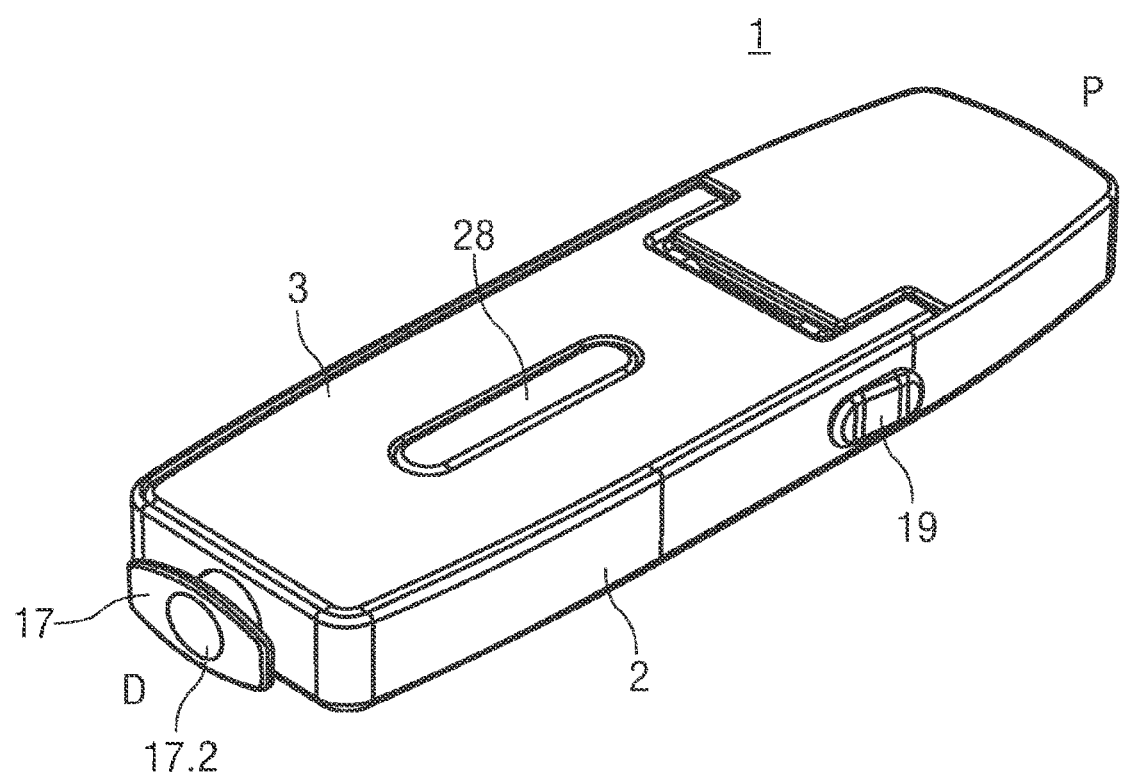
FIG. 8 is a perspective view of an exemplary embodiment of an autoinjector according to the present disclosure prior to use.

FIG. 8 shows an exemplary embodiment of an autoinjector 1 according to the present disclosure prior to use. The door 3 is locked in the closed position, because the door hook 3.1 engages the pin 19.1 on the door lock 19. The interlock sleeve 17 is in the extended position.

Figure 9:
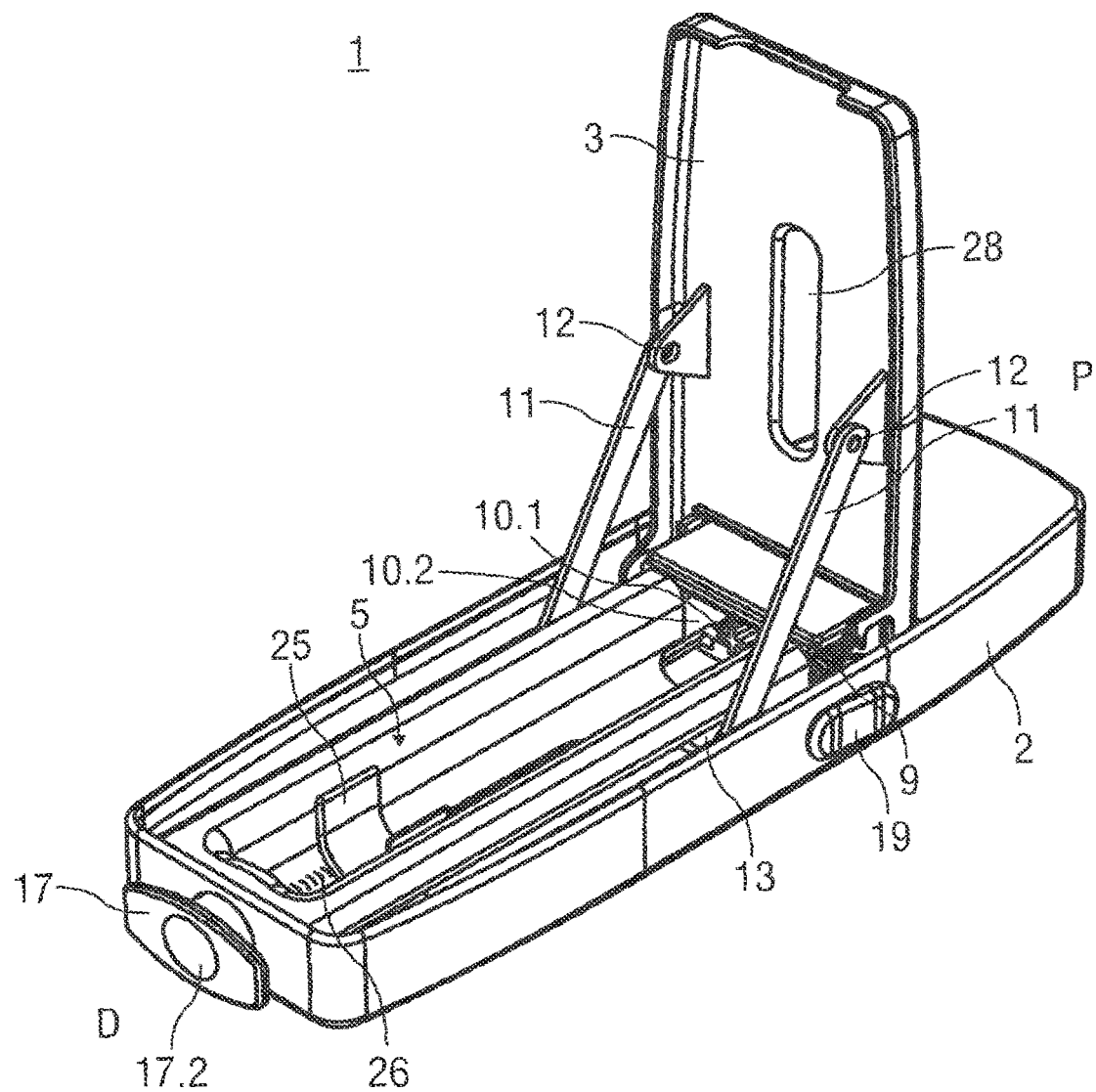
FIG. 9 is a perspective view of an exemplary embodiment of an autoinjector according to the present disclosure prior to use.

FIG. 9 shows an exemplary embodiment of an autoinjector 1 according to the present disclosure prior to use, with the door 3 in the open position. When the door lock 19 is moved from the distal position to the proximal position, the pin 19.1 disengages the door hook 3.1, and a spring may rotate the door 3 from the closed position. In an exemplary embodiment, the spring may be forceful enough to move the door 3 to the open position, or the spring may rotate the door 3 from the closed position and a user may be required to rotate the door 3 to the full open position, as shown in FIG. 9.

When the door 3 is moved from the closed position to the open position, the rollers 13 move proximally along the respective tracks 14, pushing the legs 10.2 and, thus, the plunger 10 proximally, which compresses the drive springs 9. When the door 3 is in the open position, the distal-most teeth on the ratchet face 10.5 of the legs 10.1 engage the hook 15.1 on the resilient tongue 15. As explained above, the teeth on the ratchet face 10.5 engaging the hook 15.1 prevent the plunger 10 from moving distally when the door 3 is being opened.

Figure 10:
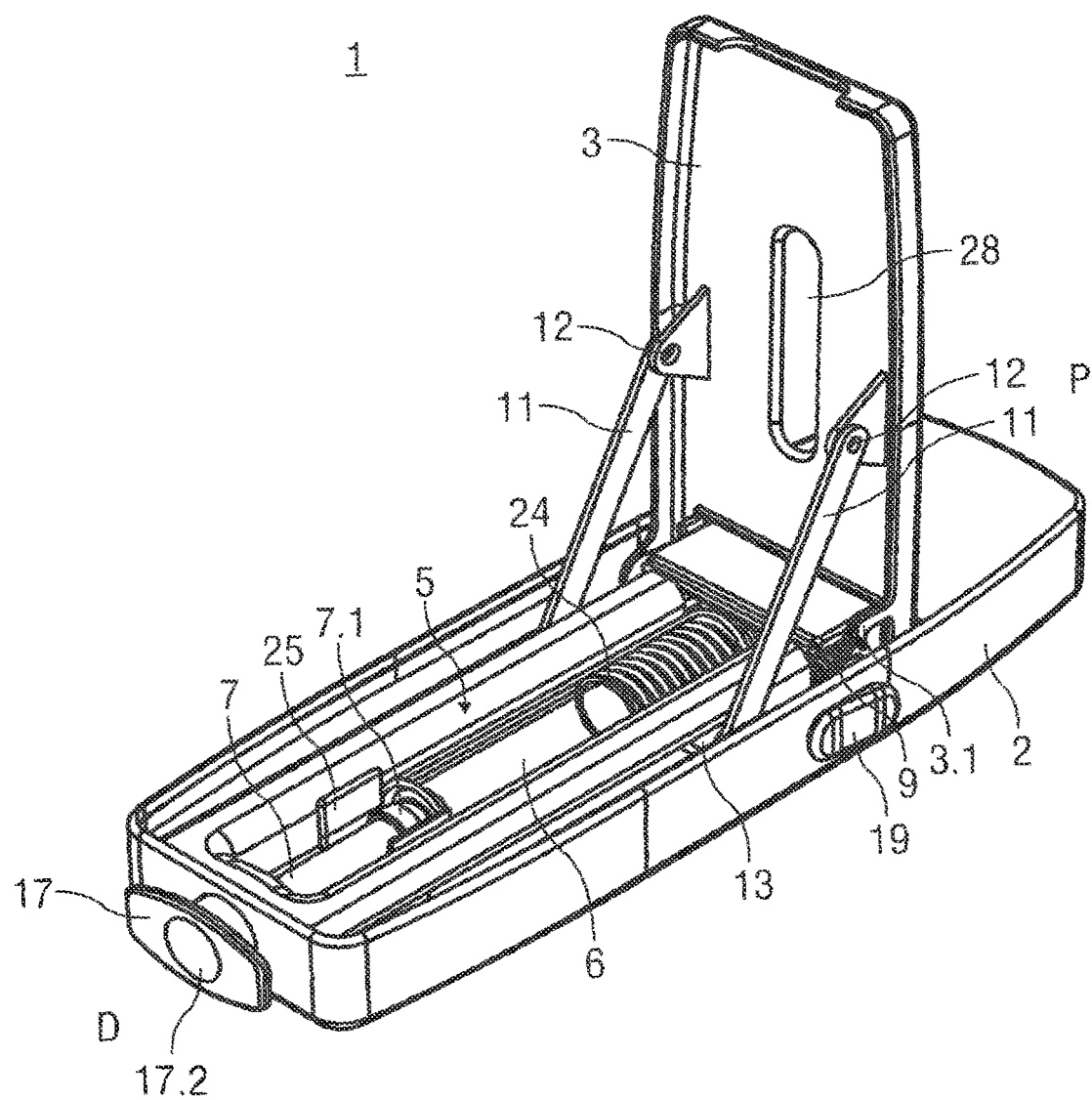
FIG. 10 is a perspective view of an exemplary embodiment of an autoinjector according to the present disclosure prior to use.

FIG. 10 shows an exemplary embodiment of an autoinjector 1 according to the present disclosure prior to use with a syringe 6. In the exemplary embodiment, the syringe 6 is placed in a syringe carrier which is slidably disposed in the case 2 or in a channel in the case 2 which allows the syringe 6 to translate relative to the case 2. The syringe 6 may be aligned such that the annular boot collar 7.1 on the needle boot 7 engages the flange on the retraction collar 25.

Figure 11:
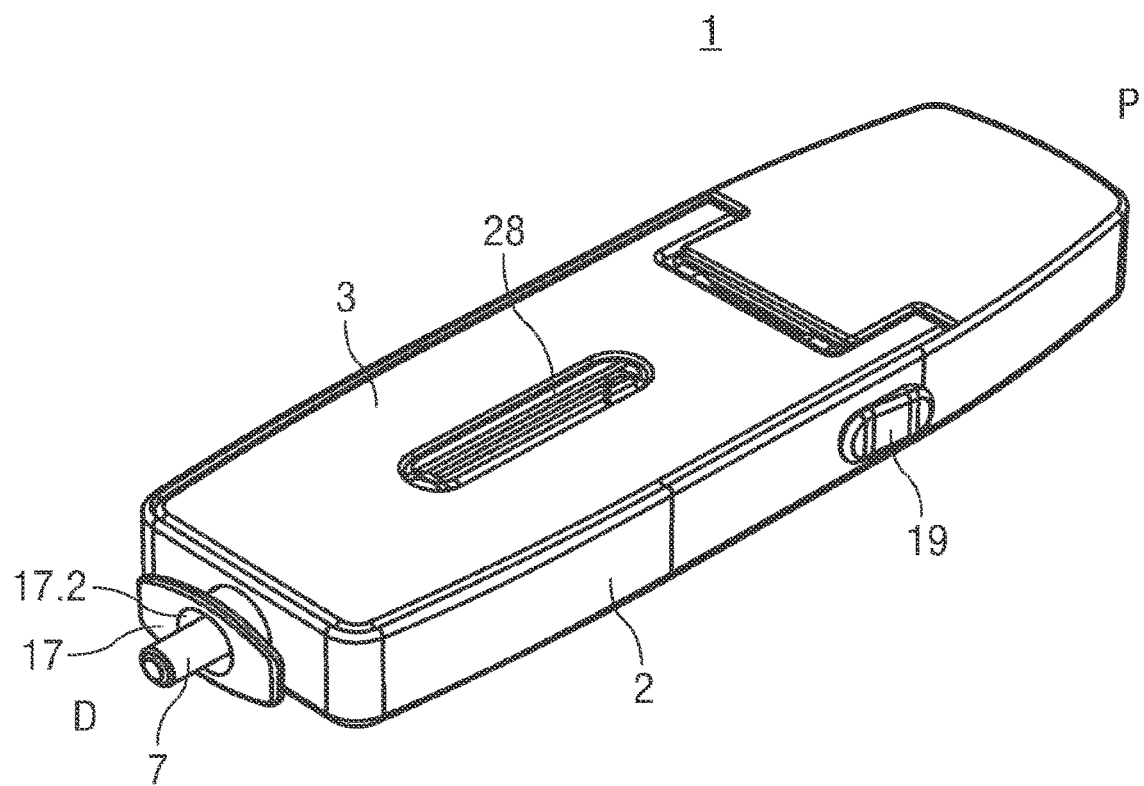
FIG. 11 is a perspective view of an exemplary embodiment of an autoinjector according to the present disclosure during use.

FIG. 11 shows an exemplary embodiment of an autoinjector 1 according to the present disclosure with an unused syringe 6 in the case 2 and the door 3 in the closed position. As the door 3 is moved from the open position to the closed position, when the door 3 is almost closed, the levers 11 and/or the rollers 13 may operably engage the retraction collar 25 to advance the retraction collar 25 in the distal direction, against the force of the retraction spring 26. Thus, when the door 3 is in the closed position, the needle boot 7 may be at least partially disengaged from the needle 22 and at least partially exposed through the aperture 17.2 in the distal end of the interlock sleeve 17. The user may then grip the needle boot 7 and pull it off the needle 22, which may remain covered by the interlock sleeve 17. When the interlock sleeve 17 is in the extended position, the trigger button of the autoinjector 1 is locked, because the trigger button beams 16 abut the interlock beams 17.1.

Figure 12:
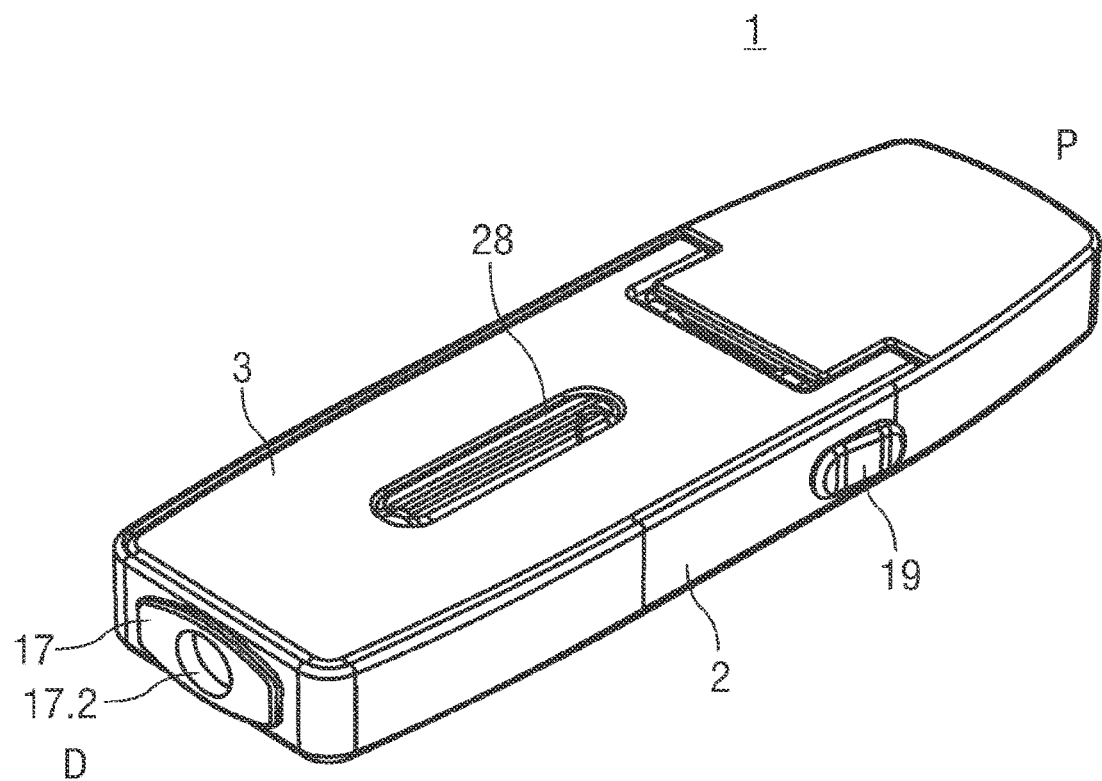
FIG. 12 is a perspective view of an exemplary embodiment of an autoinjector according to the present disclosure during use.

FIG. 12 shows an exemplary embodiment of an autoinjector 1 according to the present disclosure during use, when the autoinjector 1 has been pressed against an injection site. When the autoinjector 1 is pressed against an injection site, the interlock sleeve 17 translates in the proximal direction relative to the case 2. As the interlock sleeve 17 translates proximally relative to the case 2, the interlock beams 17.2 engage the button locking beams 18, causing the button locking beams 18 to deflect. Because the button locking beams 18 are deflected, they no longer prevent the trigger button beams 16 from moving distally relative to the case 2, and thus the trigger button is operable.

Figure 13:
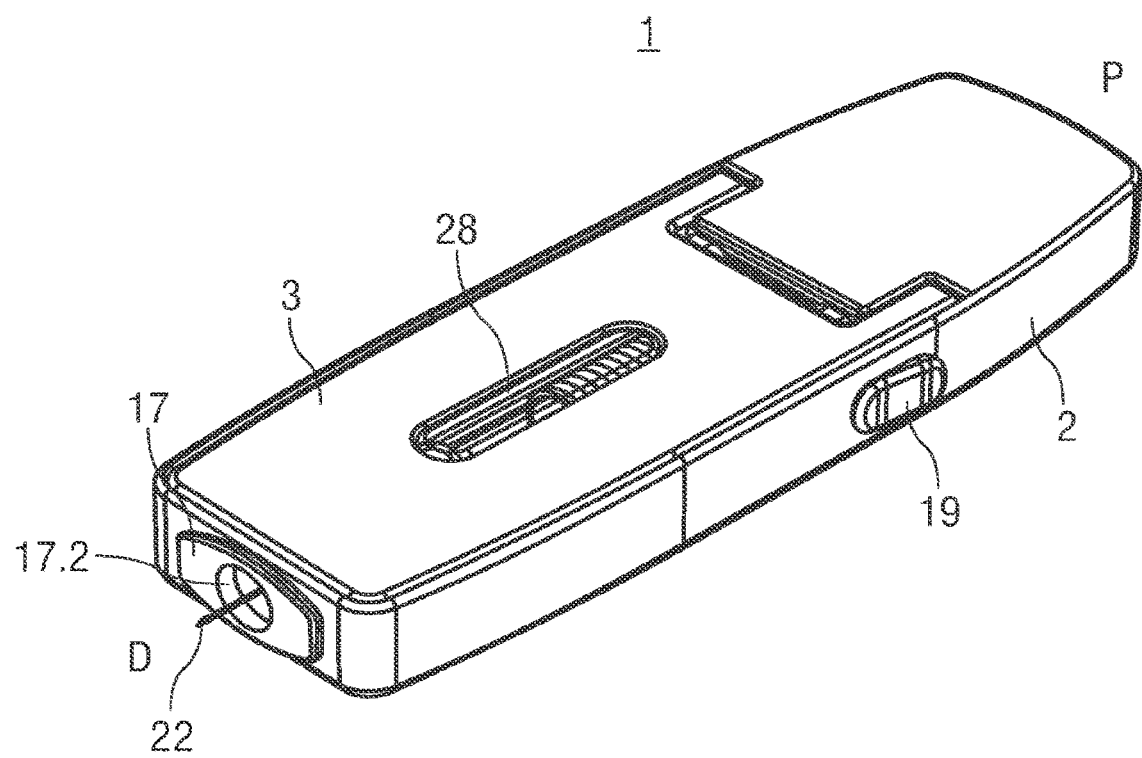
FIG. 13 is a perspective view of an exemplary embodiment of an autoinjector according to the present disclosure during use.

FIG. 13 shows an exemplary embodiment of an autoinjector 1 according to the present disclosure during use. When the trigger button is pressed, the trigger button beams 16 move distally relative to the case 2, and deflect the tongues 15. When the tongues 15 are deflected, the hook 15.1 disengages the ratchet faces 10.5 of the legs 10.2, and the plunger 10, under the force of the drive springs 9, moves distally relative to the case 2. As the plunger 10 moves distally relative to the case 2, it first engages the syringe 6 (or the syringe carrier) and pushes the syringe 6 distally relative to the case 2 for insertion of the needle 22 into the injection site. The needle 22 passes through the aperture 17.2 in the interlock sleeve 17, as shown in FIG. 13. When the syringe 6 (or the syringe carrier) abuts a first stop in the case 2, the remaining force in the drive springs 10 causes the plunger 10 to engage and push the stopper 8 in the syringe 6, dispensing the medicament in the syringe 6. In an exemplary embodiment, the plunger 10 may engage a second stop in the case 2 to limit its movement relative to the syringe 6 after the syringe 6 has engaged the first stop.

In an exemplary embodiment, the autoinjector 1 may include one or more feedback mechanisms which provide visual, audible and/or tactile feedback regarding progress of the injection. For example, when the hook 15.1 disengages the ratchet face 10.5, a clicking sound may be generated to notify the user that the injection has begun. Visual feedback may be provided, for example, through the window(s) 28 in the case 2.

Figure 19A:
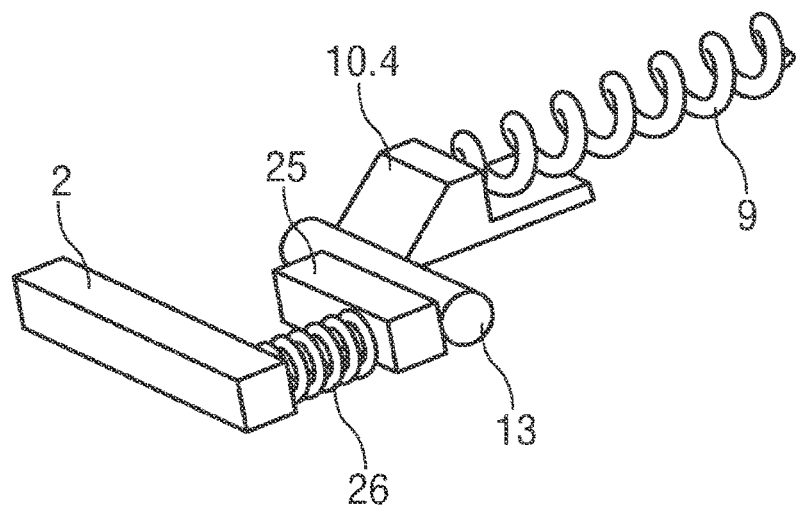
FIGS. 19A-B are perspective views of an exemplary embodiment of a syringe retraction mechanism according to the present disclosure.
Figure 19B:
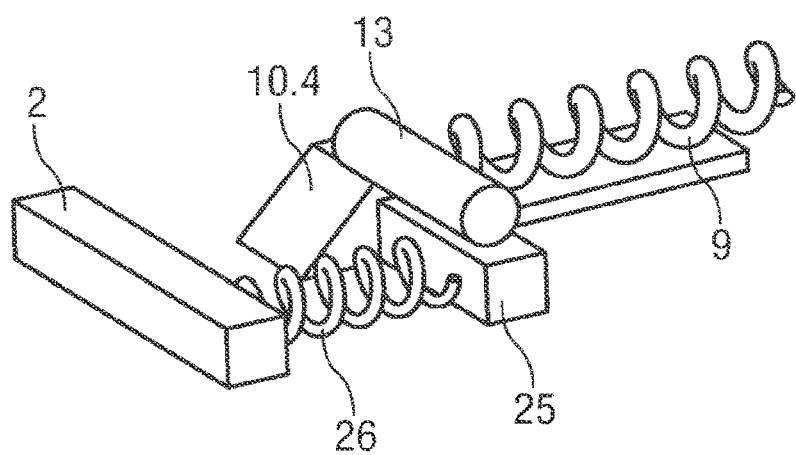
Figure 20A:
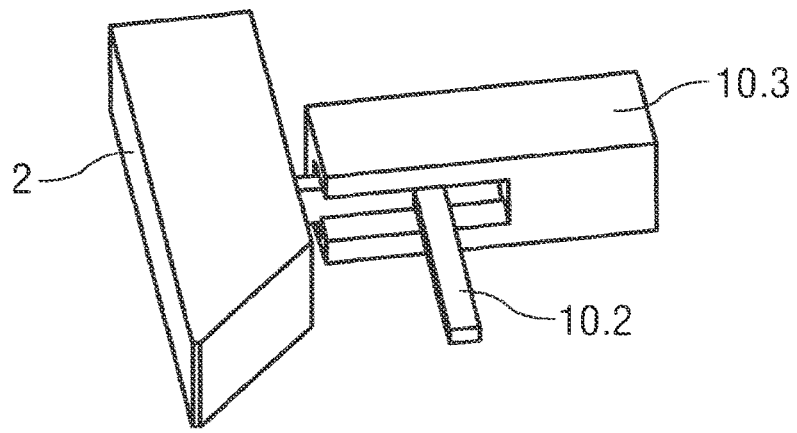
FIGS. 20A-B are perspective views of an exemplary embodiment of a drive release mechanism according to the present disclosure.
Figure 20B:
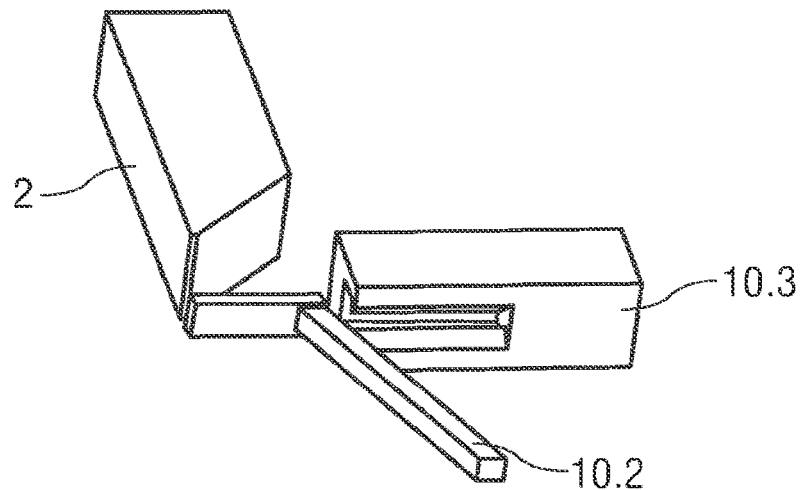

When the syringe 6 (or the syringe carrier) abuts the stop in the case 2, the retraction spring 26 has been compressed. As shown in FIGS. 19A and 19B, the retraction collar 25 is held in place by the roller 13. After activation the distal foot 10.4 contacts the roller 13 (FIG. 19A) and the ramped face of the distal foot 10.4 lifts the roller 13 to a plane above the initial contact point of the roller 13 and the retraction collar 25 (FIG. 19B). This allows the retraction spring 26 to drive the syringe 6 back in the proximal direction. Simultaneously, as transverse beam 10.3 reaches its end stop, the legs 10.2 align with a gap in the case 2 allowing them to spring out and uncouple the transverse beam 10.3 from the drive springs 9, as shown in FIGS. 20A and 20B.

Figure 14:
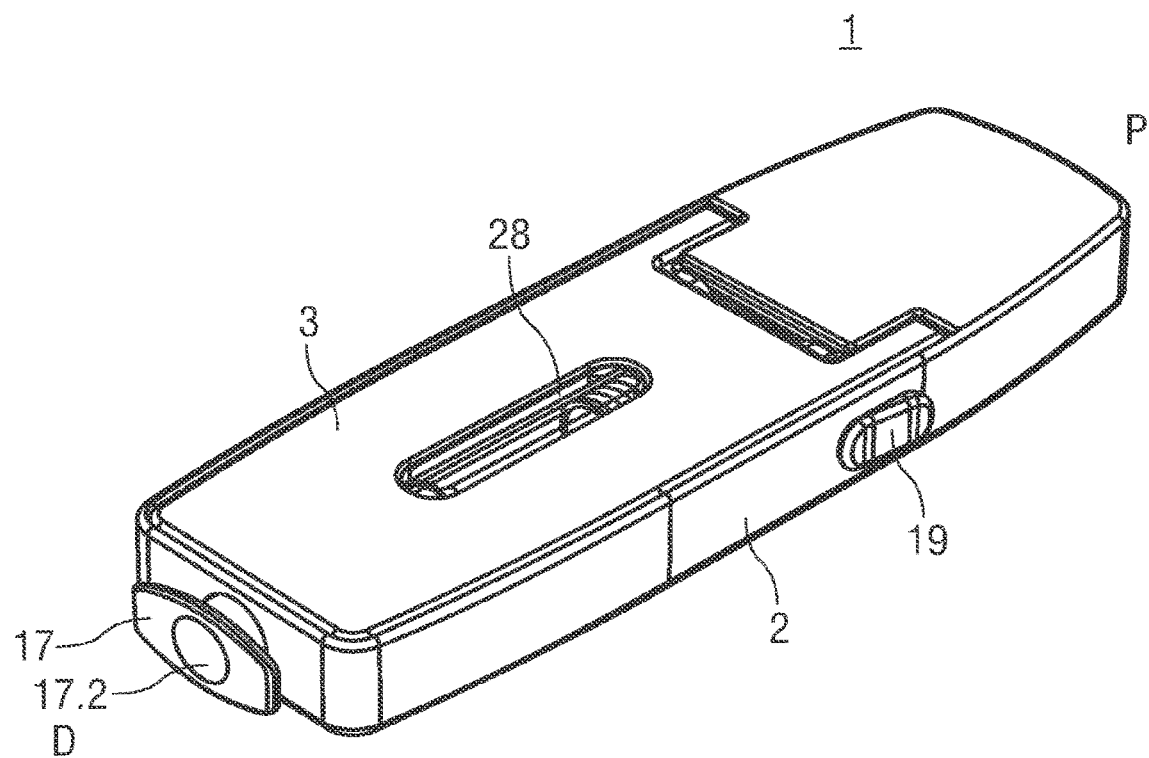
FIG. 14 is a perspective view of an exemplary embodiment of an autoinjector according to the present disclosure after use.
Figure 15:
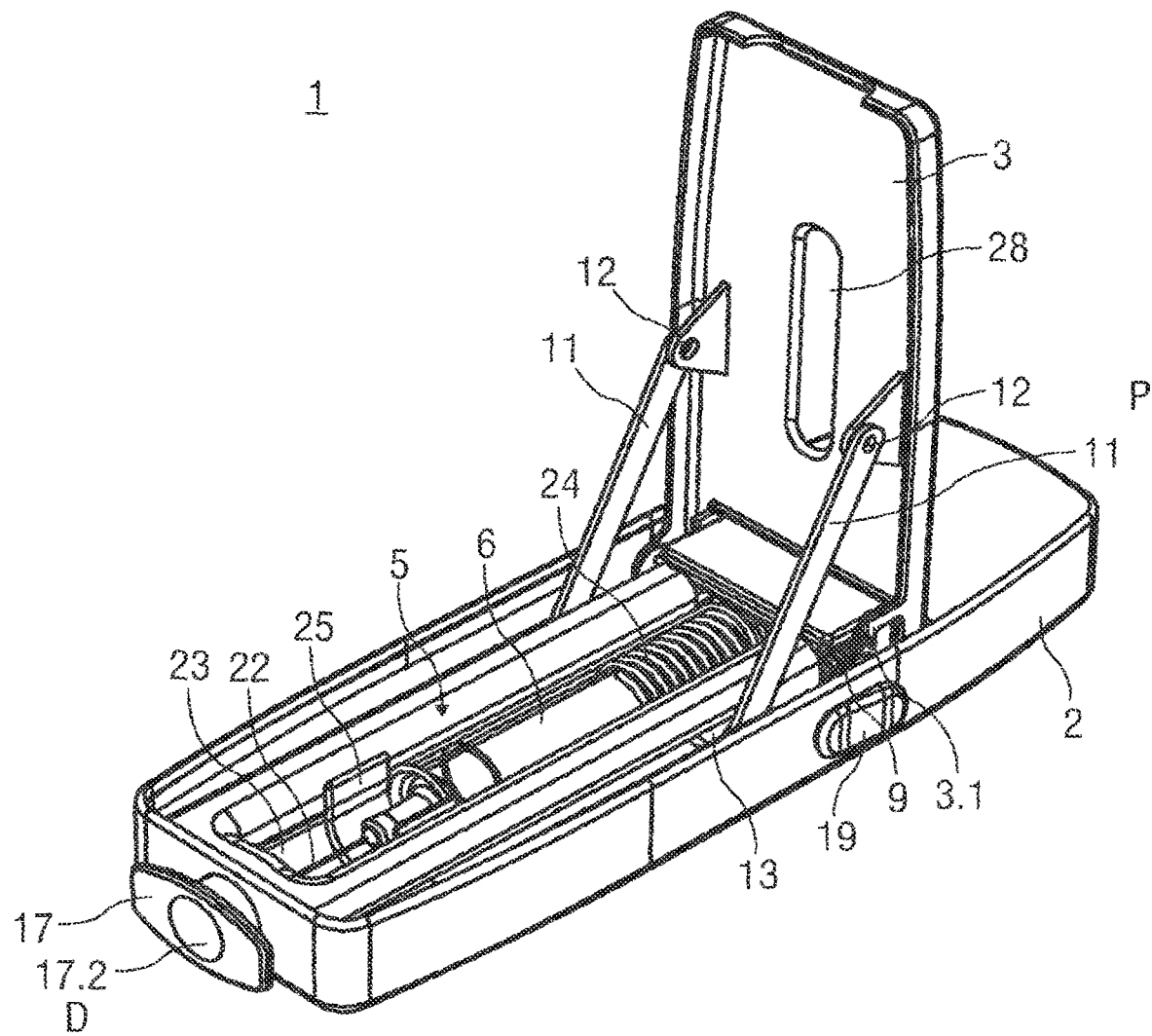
FIG. 15 is a perspective view of an exemplary embodiment of an autoinjector according to the present disclosure after use.

FIG. 14 shows an exemplary embodiment of an autoinjector 1 according to the present disclosure after use. When the autoinjector 1 is removed from the injection site (e.g., after a dose of the medicament has been delivered or for any other reason), the interlock sleeve 17 returns to the extended state under the force of the spring, the retraction spring 26 exerts force on the syringe 6 (or the syringe carrier) to withdraw the needle 22 from the injection site, and, because the trigger button has been released, the ratchet faces 10.5 engage the legs 10.2 to maintain the plunger in position relative to the case 2. For example, if the autoinjector 1 is removed from the injection site prior to delivery of the full dose of the medicament, the ratchet faces 10.5 may engage the hooks 15.1 to prevent the plunger 10 from further advancing the stopper 8. Also, after the syringe 6 has been retracted, the needle shield 23 is advanced to and locked in the extended position by the needle shield spring 24, as shown in FIG. 15. Thus, when the door 3 is unlocked (via the door lock 19) and moved to the open position, the needle 22 is covered by the locked needle shield 23 and does not present risk of needle stick injury.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

The invention claimed is:

1. An autoinjector comprising:
 a case configured to receive a syringe;
 a slidable member that is movable axially within the case to cause at least a portion of the syringe to move axially when the syringe is disposed within the case for dispensing a medicament through a needle of the syringe;
 a locking member configured to prevent actuation of the slidable member when the autoinjector is in a pre-dispense configuration;
 a sleeve coupled to a distal end of the case and surrounding at least a portion of a needle of the syringe when the syringe is disposed within the case;
 an elongate member extending proximally from the sleeve and configured to deflect the locking member to allow actuation of the plunger;
 two drive springs coupled to the slidable member and configured to apply a biasing force that acts on the slidable member to move the slidable member distally within the case, wherein the two drive springs are parallel to each other and are parallel to a distal direction;
 a door hingedly coupled to the case and adjustable between an open position and a closed position; and
 a linkage that couples the door to the case.

2. The autoinjector of claim 1, wherein the sleeve is configured to allow push-actuation of the autoinjector when the sleeve is pushed against an injection site.

3. The autoinjector of claim 1, wherein the sleeve is slidable relative to the case between:
 a retracted position in which the sleeve is contained within the case along a majority of its length, and
 an extended position in which the sleeve extends distally from the case by a distance greater than which it extends in the retracted position.

4. The autoinjector of claim 3, wherein the extended position of the sleeve corresponds to the pre-dispense configuration of the autoinjector.

5. The autoinjector of claim 4, wherein a distal end of the locking member has a first ramped surface, wherein a proximal end of the elongate member has a second ramped surface, and wherein the first and second ramped surfaces abut each other when the autoinjector is in the pre-dispense configuration.

6. The autoinjector of claim 1, wherein the elongate member is configured to deflect the locking member when the sleeve is pushed against the injection site.

7. The autoinjector of claim 6, wherein deflection of the locking member allows the slidable member to move in the distal direction under the biasing force of the two drive springs.

8. The autoinjector of claim 1, wherein a distal end of the locking member has a first ramped surface, wherein a proximal end of the elongate member has a second ramped surface, and wherein the first and second ramped surfaces abut each other when the autoinjector is in the pre-dispense configuration.

9. The autoinjector of claim 1, wherein at least one of the two drive springs comprises a tension spring.

10. The autoinjector of claim 1, wherein a distal end of the locking member has a first ramped surface, wherein a proximal end of the elongate member has a second ramped surface, and wherein the first and second ramped surfaces abut each other when the autoinjector is in the pre-dispense configuration, wherein the elongate member is configured to deflect the locking member when the sleeve is pushed against the injection site, wherein deflection of the locking member allows the slidable member to move in the distal direction under the biasing force of the two drive springs, and wherein at least one of the two drive springs comprises a tension spring.

11. The autoinjector of claim 1, wherein the linkage is further coupled to at least one of the two drive springs.

12. The autoinjector of claim 11, wherein the door is biased to the open position, and wherein the door is configured to be maintained in the closed position.

13. The autoinjector of claim 1, wherein the door is biased to the open position.

14. The autoinjector of claim 1, wherein the door is configured to be maintained in the closed position.

15. The autoinjector of claim 1, further comprising a collar that is configured to engage a needle boot of the syringe when the syringe is disposed within the case.

16. The autoinjector of claim 1, further comprising one or more user feedback mechanisms associated with an injection.

17. The autoinjector of claim 1, further comprising one or more of a visual feedback associated with an injection and an audible feedback associated with the injection.

18. An autoinjector comprising:
a case configured to receive a syringe;
a slidable member that is movable axially within the case to cause at least a portion of the syringe to move axially when the syringe is disposed within the case for dispensing a medicament through a needle of the syringe;
a locking member configured to prevent actuation of the slidable member when the autoinjector is in a pre-dispense configuration a sleeve coupled to a distal end of the case and surrounding at least a portion of a needle of the syringe when the syringe is disposed within the case;
an elongate member extending proximally from the sleeve and configured to deflect the locking member to allow actuation of the plunger;
two drive springs coupled to the slidable member and configured to apply a biasing force that acts on the slidable member to move the slidable member distally within the case, wherein the two drive springs are parallel to each other and are parallel to a distal direction;
a door hingedly coupled to the case and adjustable between an open position and a closed position;
a linkage that couples the door to the case; and
a collar that is configured to engage a needle boot of the syringe when the syringe is disposed within the case,
wherein the elongate member is configured to deflect the locking member when the sleeve is pushed against the injection site,
wherein deflection of the locking member allows the slidable member to move in the distal direction under the biasing force of the two drive springs,
wherein the locking member has a first ramped surface, wherein the elongate member has a second ramped surface, and wherein the first and second ramped surfaces abut each other when the autoinjector is in the pre-dispense configuration, and
wherein at least one of the two drive springs comprises a tension spring.

19. A system comprising:
a syringe containing a medicament; and
an autoinjector comprising:
a case configured to receive the syringe;
a slidable member that is movable axially within the case to cause at least a portion of the syringe to move axially when the syringe is disposed within the case for dispensing the medicament through a needle of the syringe;
a locking member configured to prevent actuation of the slidable member when the autoinjector is in a pre-dispense configuration;
a sleeve coupled to a distal end of the case and surrounding at least a portion of a needle of the syringe when the syringe is disposed within the case;
an elongate member extending proximally from the sleeve and configured to deflect the locking member to allow actuation of the slidable member;
two drive springs coupled to the slidable member and configured to apply a biasing force that acts on the slidable member to move the slidable member distally within the case, wherein the two drive springs are parallel to each other and are parallel to a distal direction;
a door hingedly coupled to the case and adjustable between an open position and a closed position; and
a linkage that couples the door to the case.

20. The system of claim 19, further comprising a data storage device configured to store data related to one or more of the medicament, the autoinjector, a patient, and an indicator.

21. The system of claim 20, wherein the data storage device is configured to transmit the data wirelessly or in a wired manner to a computing device.

22. The system of claim 21, wherein the needle shroud is configured to be locked in an extended position relative to the syringe barrel following a dispense of the medicament from the needle, and wherein the sleeve is configured to extend proximally from the case following a dispense of the medicament from the needle.

23. The system of claim 19, wherein the syringe comprises a syringe barrel and a needle shroud that is coupled telescopically to the syringe barrel.

24. The system of claim 23, wherein the needle shroud is spring-actuated.

25. The system of claim 23, wherein the needle shroud is configured to be locked in an extended position relative to the syringe barrel following a dispense of the medicament from the needle.

26. The system of claim 19, wherein the sleeve is configured to extend proximally from the case following a dispense of the medicament from the needle.

27. The system of claim 19, wherein the elongate member is configured to deflect the locking member when the sleeve is pushed against the injection site, and wherein deflection of the locking member allows the slidable member to move in the distal direction under the biasing force of the two drive springs.

28. The system of claim 19, wherein at least one of the two drive springs comprises a tension spring.

29. A system comprising:
a syringe containing a medicament; and
an autoinjector comprising:
a case configured to receive the syringe;
a slidable member that is movable axially within the case to cause at least a portion of the syringe to move axially when the syringe is disposed within the case for dispensing the medicament through a needle of the syringe;
a locking member configured to prevent actuation of the slidable member when the autoinjector is in a pre-dispense configuration;
a sleeve coupled to a distal end of the case and surrounding at least a portion of a needle of the syringe when the syringe is disposed within the case;
an elongate member extending proximally from the sleeve and configured to deflect the locking member to allow actuation of the plunger;
two drive springs coupled to the slidable member and configured to apply a biasing force that acts on the slidable member to move the slidable member distally within the case, wherein the two drive springs are parallel to each other and are parallel to a distal direction;
a door hingedly coupled to the case and adjustable between an open position and a closed position; and
a linkage that couples the door to the case;
wherein the elongate member is configured to deflect the locking member when the sleeve is pushed against the injection site, wherein deflection of the locking member allows the slidable member to move in the distal direction under the biasing force of the two drive springs, wherein the locking member has a first ramped surface, wherein the elongate member has a second ramped surface, and wherein the first and second ramped surfaces abut each other when the autoinjector is in the pre-dispense configuration, and wherein at least one of the two drive springs comprises a tension spring.

\* \* \* \* \*